United States Patent
Olson

(10) Patent No.: US 10,448,995 B2
(45) Date of Patent: *Oct. 22, 2019

(54) SYSTEM AND METHOD FOR CONTROLLING DELIVERY OF ABLATION ENERGY TO TISSUE

(71) Applicant: St. Jude Medical, Atrial Fibrillation Division, Inc., St. Paul, MN (US)

(72) Inventor: Eric Steven Olson, Maplewood, MN (US)

(73) Assignee: St. Jude Medical, Atrial Fibrillation Division, Inc., St. Paul, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/052,034

(22) Filed: Aug. 1, 2018

(65) Prior Publication Data

US 2019/0021790 A1 Jan. 24, 2019

Related U.S. Application Data

(63) Continuation of application No. 15/465,112, filed on Mar. 21, 2017, now Pat. No. 10,052,153, which is a
(Continued)

(51) Int. Cl.
*A61B 18/14* (2006.01)
*A61B 18/00* (2006.01)
*A61B 90/00* (2016.01)

(52) U.S. Cl.
CPC ............. *A61B 18/1492* (2013.01); *A61B 2018/00577* (2013.01); *A61B 2018/00666* (2013.01);
(Continued)

(58) Field of Classification Search
USPC ........................................ 606/14, 34, 174
See application file for complete search history.

(56) References Cited

U.S. PATENT DOCUMENTS

| 5,341,807 A | 8/1994 | Nardella |
| 7,263,397 B2 | 8/2007 | Hauck et al. |

(Continued)

FOREIGN PATENT DOCUMENTS

| EP | 1810630 A1 | 7/2007 |
| WO | 1996000036 A1 | 1/1996 |

(Continued)

OTHER PUBLICATIONS

Deneke, Thomas et al., "Contact Detection and Power Control of Radiofrequency Ablation Using Tissue Interface Temp During Periods of Intermitted Contact," 2011 Conference of the Heart Rhythm Society, Abstract, (May 5, 2011).
(Continued)

*Primary Examiner* — Nicole F Lavert
(74) *Attorney, Agent, or Firm* — Dykema Gossett PLLC

(57) ABSTRACT

A system for controlling delivery of ablation energy by an ablation catheter to tissue in a body is provided. The system includes an electronic control unit configured to determine, responsive to a measurement signal from the ablation catheter, a value for a characteristic associated with the delivery of ablation energy to the tissue. In one embodiment, the characteristic is the degree of contact between the ablation catheter and the tissue. The unit is further configured to generate a control signal, responsive to the determined value of the characteristic, to control an amount of energy delivered from an ablation delivery element on the ablation catheter to the tissue. The amount of energy varies in response to the determined value of the characteristic when the determined value of the characteristic meets a predetermined condition relative to a threshold value for the characteristic.

22 Claims, 5 Drawing Sheets

Related U.S. Application Data continuation of application No. 14/922,986, filed on Oct. 26, 2015, now Pat. No. 9,597,148, which is a continuation of application No. 13/826,227, filed on Mar. 14, 2013, now Pat. No. 9,179,972.

(60) Provisional application No. 61/642,979, filed on May 4, 2012.

(52) U.S. Cl.
CPC ........... *A61B 2018/00702* (2013.01); *A61B 2018/00791* (2013.01); *A61B 2018/00839* (2013.01); *A61B 2018/00875* (2013.01); *A61B 2090/065* (2016.02)

(56) References Cited

U.S. PATENT DOCUMENTS

| | | | |
|---|---|---|---|
| 7,386,339 | B2 | 6/2008 | Strommer et al. |
| 7,857,810 | B2 | 12/2010 | Wang et al. |
| 2007/0100332 | A1 | 5/2007 | Paul et al. |
| 2007/0123764 | A1 | 5/2007 | Thao |
| 2008/0015568 | A1 | 1/2008 | Paul |
| 2008/0161796 | A1 | 7/2008 | Cao |
| 2008/0249522 | A1 | 10/2008 | Pappone |
| 2008/0275428 | A1 | 11/2008 | Tegg et al. |
| 2009/0138011 | A1* | 5/2009 | Epstein ............. A61B 18/1233 606/42 |
| 2009/0163904 | A1 | 6/2009 | Miller et al. |
| 2009/0171338 | A1 | 7/2009 | Olson |
| 2009/0247942 | A1 | 10/2009 | Kirschenman |
| 2009/0247944 | A1 | 10/2009 | Kirschenman |
| 2009/0247993 | A1 | 10/2009 | Kirschenman |
| 2009/0248042 | A1 | 10/2009 | Kirschenman |
| 2010/0069921 | A1 | 3/2010 | Miller |
| 2010/0106158 | A1 | 4/2010 | Sato |
| 2010/0168735 | A1 | 7/2010 | Deno |
| 2010/0211062 | A1 | 8/2010 | Stockert |
| 2010/0228247 | A1 | 9/2010 | Paul |
| 2010/0256558 | A1 | 10/2010 | Olson |
| 2011/0015569 | A1 | 1/2011 | Kirschenman |
| 2011/0022045 | A1 | 1/2011 | Cao |
| 2012/0101413 | A1* | 4/2012 | Beetel ............... A61B 18/082 601/3 |

FOREIGN PATENT DOCUMENTS

| | | |
|---|---|---|
| WO | 2009120982 A1 | 10/2009 |
| WO | 2010078453 A1 | 7/2010 |

OTHER PUBLICATIONS

Manufacturer: Stockert GmbH, Freiburg, Germany Title: Stockert 70 Radiofrequency Generator User Manual Published: Jun. 26, 2000.

\* cited by examiner

SYSTEM AND METHOD FOR CONTROLLING DELIVERY OF ABLATION ENERGY TO TISSUE

CROSS-REFERENCE TO RELATED APPLICATIONS

This application is a continuation of U.S. application Ser. No. 15/465,112, filed 21 Mar. 2017 (the '112 application), now U.S. Pat. No. 10,052,153, which in turn claims the benefit of U.S. application Ser. No. 14/922,986, filed 26 Oct. 2015, (the '986 application), now U.S. Pat. No. 9,597,148, which in turn claims the benefit of U.S. application Ser. No. 13/826,227, filed 14 Mar. 2013 (the '227 application), now U.S. Pat. No. 9,179,972, which in turn claims the benefit of U.S. provisional application No. 61/642,979, filed 4 May 2012 (the '979 application). The '112 application, the '986 application, the '227 application, and the '979 application are each hereby incorporated by reference as though fully set forth herein.

BACKGROUND OF THE INVENTION a. Field of the Invention

This invention relates to a system and method for controlling delivery of ablation energy by an ablation catheter to tissue in a body. In particular, the instant invention relates to a system and method that enable fine control or titration of the delivery of ablation energy to tissue in response to changes in various characteristics associated with the delivery of ablation energy to the tissue such as the degree of contact between the ablation catheter and tissue.

b. Background Art

It is well known to use ablation catheters to create tissue necrosis in cardiac tissue to correct cardiac arrhythmias (including, but not limited to, atrial fibrillation, atrial flutter, atrial tachycardia and ventricular tachycardia). Arrhythmia can create a variety of dangerous conditions including irregular heart rates, loss of synchronous atrioventricular contractions and stasis of blood flow which can lead to a variety of ailments and even death. It is believed that the primary cause of many arrhythmias is stray electrical signals within one or more heart chambers. The ablation catheter imparts ablative energy (e.g., radiofrequency energy, light energy, ultrasound, or thermal (cryo or heat based) energy) to the heart tissue to create a lesion in the heart tissue. This lesion disrupts undesirable electrical pathways and thereby limits or prevents stray electrical signals that lead to arrhythmias.

Ablation therapy provides significant benefits in resolving cardiac arrhythmias. There are, however, a number of risks associated with ablation therapy. The use of certain types of ablative energy (e.g. radiofrequency energy) generates heat that can lead to formation of a thrombus at or near the distal tip of the catheter. If the thrombus becomes dislodged, there is a risk that the thrombus will travel to a location where the thrombus will prevent further bloodflow and result in stroke. Many catheters employ saline irrigation to cool the tip of the catheter, but irrigation may fail to sufficiently reduce heat and thrombus formation. Thrombii may also be removed by employing vacuum force through the sheath in which the catheter is disposed or by removing the catheter itself, but both of these actions may result in dislodgement of the thrombus.

The foregoing discussion is intended only to illustrate the present field and should not be taken as a disavowal of claim scope.

BRIEF SUMMARY OF THE INVENTION

Among other things, various embodiments are directed to a system and method for controlling delivery of ablation energy by an ablation catheter to tissue in a body. In particular, system(s) and method(s) are disclosed that improve control of the delivery of ablation energy to minimize delivery of energy into the blood and reduce the incidence of thrombus formation during a procedure.

A system for controlling delivery of ablation energy from an ablation catheter to tissue in a body in accordance with one embodiment of the invention may include an electronic control unit configured to determine, responsive to a measurement signal from the ablation catheter, a value for a characteristic associated with the delivery of ablation energy to the tissue. The electronic control unit is further configured to generate a first control signal, responsive to the determined value of the characteristic, to control an amount of energy delivered from the ablation delivery element to the tissue. The amount of energy varies in response to the determined value of the characteristic when the determined value of the characteristic meets a predetermined condition relative to a first threshold value for the characteristic. In accordance another embodiment of the invention, the system may further include a radio frequency generator configured to generate an ablation signal responsive to the first control signal. The ablation signal controls the amount of energy delivered from an ablation delivery element on the ablation catheter to the tissue. In accordance with yet another embodiment of the invention, the system may further include a remote catheter guidance system including a manipulator assembly and a drive assembly supported on the manipulator assembly and coupled to at least one steering wire of the ablation catheter. The electronic control unit may be further configured to generate a second control signal, responsive to the determined value of the characteristic, to control the drive assembly and movement of a distal end of the ablation catheter.

A system for controlling delivery of ablation energy from an ablation catheter to tissue in a body in accordance with another embodiment of the invention includes a computer readable storage medium having a computer program encoded thereon that when executed by an electronic control unit controls delivery of ablation energy from an ablation catheter to tissue in a body. The computer program includes code for determining, responsive to a measurement signal from the ablation catheter, a value for a characteristic associated with the delivery of ablation energy to the tissue. The computer program further includes code for generating a first control signal, responsive to the determined value of the characteristic, to control an amount of energy delivered from the ablation delivery element to the tissue. The amount of energy varies in response to the determined value for the characteristic when the determined value of the characteristic meets a predetermined condition relative to a first threshold value for the characteristic.

A system and method in accordance with the present invention is advantageous because the system and method enable finer control of the delivery of ablation energy to tissue in response to changes in various characteristics associated with the delivery of ablation energy to the tissue. As a result, delivery of ablation energy into the blood is minimized to reduce the risks of thrombus formation.

The foregoing and other aspects, features, details, utilities, and advantages of the present invention will be apparent from reading the following description and claims, and from reviewing the accompanying drawings.

DETAILED DESCRIPTION OF EMBODIMENTS OF THE INVENTION

Various embodiments are described herein of various apparatuses, systems, and/or methods. Numerous specific details are set forth to provide a thorough understanding of the overall structure, function, manufacture, and use of the embodiments as described in the specification and illustrated in the accompanying drawings. It will be understood by those skilled in the art, however, that the embodiments may be practiced without such specific details. In other instances, well-known operations, components, and elements have not been described in detail so as not to obscure the embodiments described in the specification. Those of ordinary skill in the art will understand that the embodiments described and illustrated herein are non-limiting examples, and thus it can be appreciated that the specific structural and functional details disclosed herein may be representative and do not necessarily limit the scope of the embodiments, the scope of which is defined solely by the appended claims.

Reference throughout the specification to "various embodiments," "some embodiments," "one embodiment," or "an embodiment", or the like, means that a particular feature, structure, or characteristic described in connection with the embodiment is included in at least one embodiment. Thus, appearances of the phrases "in various embodiments," "in some embodiments," "in one embodiment," or "in an embodiment", or the like, in places throughout the specification are not necessarily all referring to the same embodiment. Furthermore, the particular features, structures, or characteristics may be combined in any suitable manner in one or more embodiments. Thus, the particular features, structures, or characteristics illustrated or described in connection with one embodiment may be combined, in whole or in part, with the features structures, or characteristics of one or more other embodiments without limitation given that such combination is not illogical or non-functional.

It will be appreciated that the terms "proximal" and "distal" may be used throughout the specification with reference to a clinician manipulating one end of an instrument used to treat a patient. The term "proximal" refers to the portion of the instrument closest to the clinician and the term "distal" refers to the portion located furthest from the clinician. It will be further appreciated that for conciseness and clarity, spatial terms such as "vertical," "horizontal," "up," and "down" may be used herein with respect to the illustrated embodiments. However, surgical instruments may be used in many orientations and positions, and these terms are not intended to be limiting and absolute.

Figure 1:
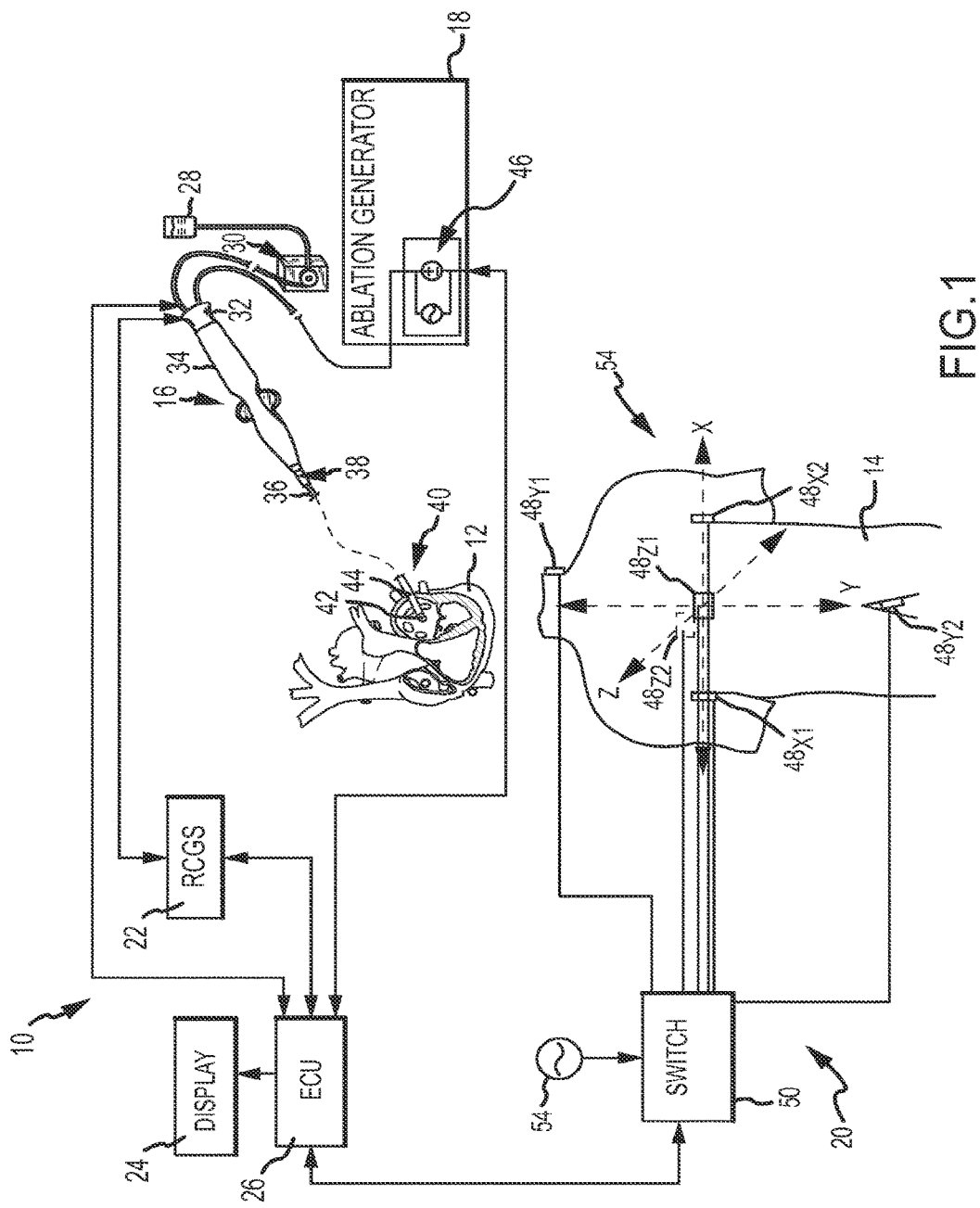
FIG. 1 is diagrammatic view of one embodiment of a system for controlling delivery of ablation energy from an ablation catheter to tissue in a body in accordance with the present teachings.

Referring now to the drawings wherein like reference numerals are used to identify identical components in the various views, FIG. 1 illustrates one embodiment of a system 10 for controlling delivery of ablation energy to tissue 12 in a body 14. In the illustrated embodiment, tissue 14 comprises cardiac tissue within a human body. It should be understood, however, that a system 10 in accordance with the present teachings may find application in connection with procedures for the diagnosis or treatment of a variety of tissues in human and on human bodies. System 10 may include an ablation catheter 16, an ablation generator 18, a medical device position and navigation system 20, a remote catheter guidance system (RCGS) 22, a display system 24, and an electronic control unit (ECU) 26.

Catheter 16 is provided for examination, diagnosis and treatment of internal body tissues such as tissue 12. In accordance with one embodiment of the invention, catheter 16 comprises an ablation catheter and, more particularly, an irrigated radio-frequency (RF) ablation catheter. It should be understood, however, that catheter 16 is provided for illustration only and that system 10 could be adapted for use with other types of ablation catheters including those providing different types of ablation energy (e.g., cryoablation, ultrasound, etc.). Catheter 16 is connected to a fluid source 28 having a biocompatible fluid such as saline through a pump 30 (which may comprise, for example, a fixed rate roller pump or variable volume syringe pump with a gravity feed supply from fluid source 28 as shown) for irrigation. Catheter 16 is also electrically connected to ablation generator 18 for delivery of RF energy. Catheter 16 may include a cable connector or interface 32, a handle 34, a shaft 36 having a proximal end 38 and a distal end 40 (as used herein, "proximal" refers to a direction toward the end of the catheter near the clinician, and "distal" refers to a direction away from the clinician and (generally) inside the body of a patient) and one or more electrodes 42, 44. Catheter 16 may also include other conventional components not illustrated herein such as a temperature sensor, additional electrodes, and corresponding conductors or leads.

Connector 32 provides mechanical, fluid and electrical connection(s) for cables extending from ablation generator 18, RCGS 22, and pump 30. Connector 32 is conventional in the art and is disposed at a proximal end of catheter 16.

Handle 34 provides a location for the clinician to hold catheter 16 and may further provides means for steering or guiding shaft 36 within body 14. For example, handle 34 may include means to change the length of a steering wire extending through catheter 16 to distal end 40 of shaft 36 to steer distal end 40 and, thus, shaft 36. Handle 34 is also conventional in the art and it will be understood that the construction of handle 34 may vary and may be absent in a fully-robotic implementation of the system.

Shaft 36 is an elongated, flexible member configured for movement within body 14. Shaft 36 supports electrodes 42, 44, associated conductors, and possibly additional electronics used for signal processing or conditioning. Shaft 36 may also permit transport, delivery, and/or removal of fluids (including irrigation fluids and bodily fluids), medicines, and/or surgical tools or instruments. Shaft 36 may be made from conventional materials such as polyurethane and defines one or more lumens configured to house and/or transport electrical conductors, fluids, or surgical tools. Shaft 36 may be introduced into a blood vessel or other structure within body 14 through a conventional introducer sheath. Shaft 36 may then be steered or guided through body 14 to a desired location such as tissue 12 using RCGS 22 or with guide wires or with pullwires or other means known in the art.

Electrodes 42, 44 are provided for a variety of diagnostic and therapeutic purposes including, for example, electrophysiological studies, catheter identification and location, pacing, and cardiac mapping and ablation. In the illustrated embodiment, catheter 16 includes an ablation tip electrode 42 at distal end 40 of shaft 36 that functions as an ablation delivery element and one or more ring electrodes 44 that may be used to obtain electrograms for tissue 12 and for other conventional purposes. It should be understood, however, that the number, orientation, and purpose of electrodes 42, 44 may vary. Additional details regarding a catheter, such as catheter 16, may be found in U.S. Pat. No. 7,857,810, the entire disclosure of which is incorporated herein by reference.

Ablation generator 18 generates, delivers and controls radiofrequency energy used by catheter 16. Generator 18 a radiofrequency generator 46 configured to generate an ablation signal that is output across a pair of source connectors: a positive polarity connector which may connect to electrode 42 on catheter 16; and a negative polarity connector which may be electrically connected by conductors or lead wires to a patch electrode (not shown) on body 14. It should be understood that the term connectors as used herein does not imply a particular type of physical interface mechanism, but is rather broadly contemplated to represent one or more electrical nodes. Generator 46 is configured to generate a signal at a predetermined frequency in accordance with one or more user specified parameters (e.g., power, time, etc.) and under the control of various feedback sensing and control circuitry as is know in the art. Generator 46 may generate a signal, for example, with a frequency of about 450 kHz or greater. Ablation generator 18 may also monitor various parameters associated with the ablation procedure including impedance, the temperature at the tip of catheter 16, ablation energy and the position of the catheter 16 and provide feedback to the physician regarding these parameters.

System 20 is provided to determine the position and orientation of catheter 16 and similar devices within body 14. System 20 may comprise the system offered for sale under the trademark EnSite™ NavX™ by St. Jude Medical, Inc. and described in U.S. Pat. No. 7,263,397, the entire disclosure of which is incorporated herein by reference. The system is based on the principle that when low amplitude electrical signals are passed through the thorax, body 14 acts as a voltage divider (or potentiometer or rheostat) such that the electrical potential or field strength measured at an electrode on catheter 16 may be used to determine the position of the electrode, and therefore catheter 16 relative to a pair of external patch electrodes using Ohm's law and the relative location of a reference electrode (e.g. in the coronary sinus). In one configuration, the system includes three pairs of patch electrodes that are placed on opposed surfaces of the body (e.g., chest and back, left and right sides of the thorax, and neck and leg) and form generally orthogonal x, y, and z axes as well as a reference electrode/patch that is typically placed near the stomach and provides a reference value and acts as the origin of the coordinate system for the navigation system. Sinusoidal currents are driven through each pair of patch electrodes and voltage measurements for one or more position sensors (e.g., electrodes) associated with the medical device are obtained. The measured voltages are a function of the distance of the position sensors from the patch electrodes. The measured voltages are compared to the potential at the reference electrode and a position of the position sensors within the coordinate system of the navigation system is determined. In accordance with this exemplary system, system 20 may include patch electrodes 48 (namely $48_{X1}$, $48_{X2}$, $48_{Y1}$, $48_{Y2}$, $48_{Z1}$, $48_{Z2}$) a switch 50, and a signal generator 52.

Patch electrodes 48 are provided to generate electrical signals used in determining the position of catheter 16 within a three dimensional coordinate system 54 of system 20. Electrodes 48 may also be used to generate EP data regarding tissue 12. Electrodes 48 are placed orthogonally on the surface of body 14 and are used to create axes specific electric fields within body 14. Electrodes $48_{X1}$, $48_{X2}$ may be placed along a first (x) axis. Similarly, electrodes $48_{Y1}$, $48_{Y2}$ may be placed along a second (y) axis, and electrodes $48_{Z1}$, $48_{Z2}$ may be placed along a third (z) axis. Each of the electrodes 48 may be coupled to multiplex switch 50. ECU 26 is configured through appropriate software to provide control signals to switch 50 and thereby sequentially couple pairs of electrodes 48 to signal generator 52. Excitation of each pair of electrodes 48 generates an electromagnetic field within body 14 and within an area of interest such as the heart. Voltage levels at non-excited electrodes 48 may be filtered and converted and provided to ECU 26 for use as reference values.

In an alternative embodiment, system 20 may comprise a system that employs magnetic fields to detect the position of catheter 16 within body 14 such as the MediGuide™ Technology offered for sale by St. Jude Medical, Inc. and generally shown and described in, for example, U.S. Pat. No. 7,386,339, the entire disclosure of which is incorporated herein by reference. In such a system, a magnetic field generator may be employed having three orthogonally arranged coils, arranged to create a magnetic field within body 14 and to control the strength, orientation, and frequency of the field. The magnetic field generator may be located above or below the patient (e.g., under a patient table) or in another appropriate location. Magnetic fields are generated by the coils and current or voltage measurements for one or more position sensors (e.g., a coil) associated with catheter 16 are obtained. The measured currents or voltages are proportional to the distance of the sensors from the coils thereby allowing a position of the sensors within the coordinate system 54 of system 20.

Figure 2:
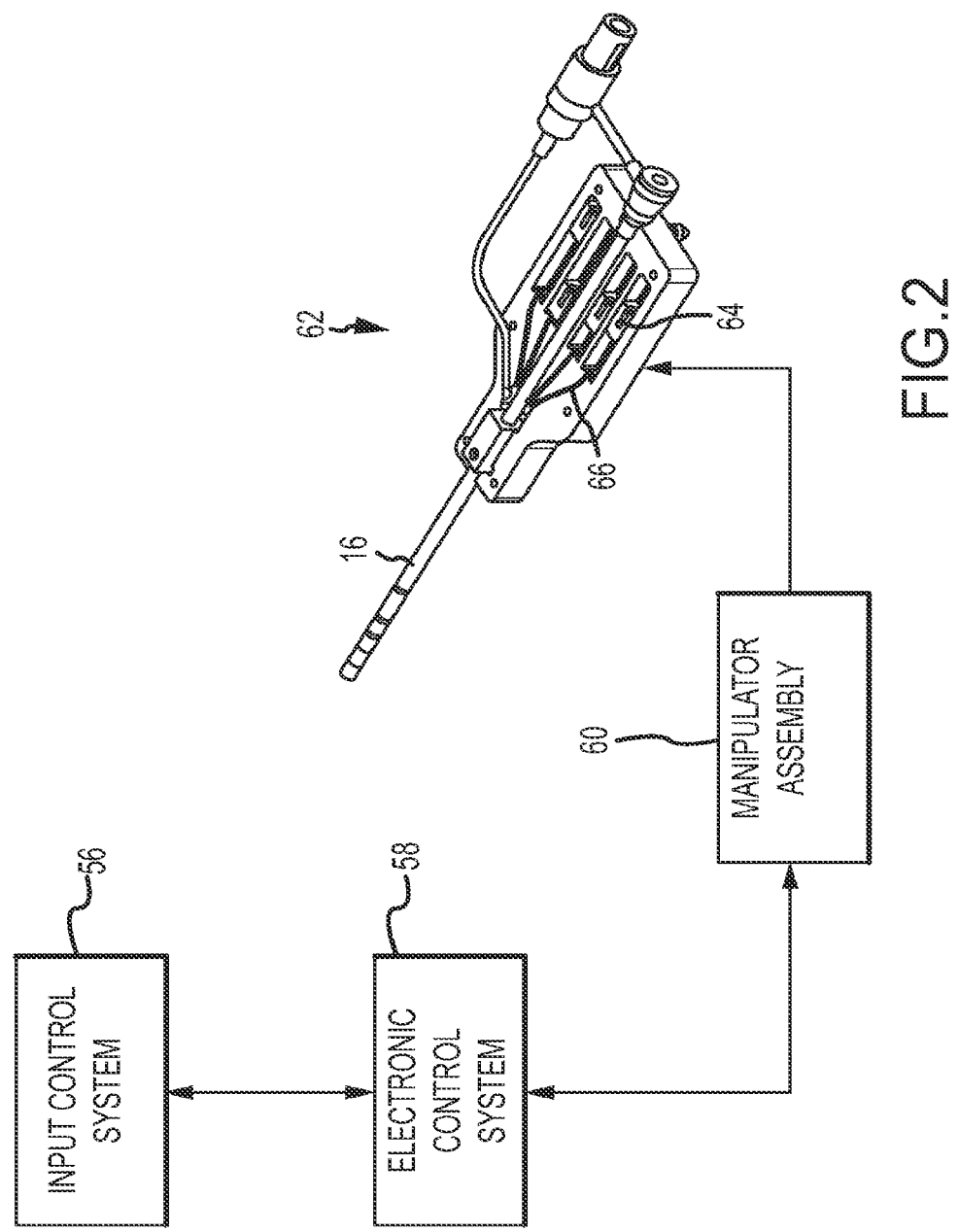
FIG. 2 is a diagrammatic view of a remote catheter guidance system for use in the system of FIG. 1.

RCGS 22 is provided to manipulate catheter 16. In particular, RCGS 22 permits control of translation, distal bending, and virtual rotation of catheter 16 and any surrounding sheath. RCGS 22 therefore provides the user with a type of control similar to that provided by conventional manually-operated systems, but allows for repeatable, precise, and dynamic movements. A clinician may identify target locations (potentially forming a path) on an image of tissue 12. RCGS 22 relates these digitally selected points to positions within the patient's actual/physical anatomy, and may thereafter command control the movement of catheter 16 to the defined positions where the clinician or the RCGS 22 can perform the desired diagnostic of therapeutic function. Referring to FIG. 2, RCGS 22 may include an input control system 56, an electronic control system 58, and a manipulator assembly 60 for operating a translation and/or deflection drive assembly or device cartridge 62.

Input control system 56 is provided to allow the clinician to interact with the RCGS 22 to control movement of catheter 16. System 56 may include, for example, instrumented traditional catheter handle controls, oversized catheter models, instrumented user-wearable gloves, touch screen display monitors, 2-D input devices, 3-D input devices, spatially detected styluses, and traditional joysticks. These input devices may be configured to directly control the movement of catheter 16 and any surrounding sheath, or may be configured, for example, to manipulate a target or cursor on an associated display.

Electronic control system 58 is configured to translate (i.e., interpret) inputs (e.g., motions) of the user at an input device or from another source into a resulting movement of catheter 16. The electronic control system 58 issues commands to manipulator assembly 60 (i.e., to the actuation units—electric motors) to move or bend catheter 16 to prescribed positions and/or in prescribed ways, all in accordance with the received user input and a predetermined programmed operating strategy. System 58 may include one or more stand-alone microprocessors or application specific integrated circuits (ASICs). Alternatively, system 58 may form a part of ECU 26.

Manipulator assembly 60 is configured to maneuver catheter 16 in response to commands from electronic control system 58. Assembly 60 may cause translational movement such as advancement or withdrawal of catheter 16 and effect deflection of distal end 40 of catheter 16 and/or rotation or virtual motion. Assembly 60 may include conventional actuation mechanisms (e.g., a plurality of electric motor and lead screw combinations) for linearly actuating one or more control members (e.g., steering wires) associated with catheter 16 for achieving the above-described translation, deflection, and/or rotation (or virtual rotation).

Drive assembly or device cartridge 62 is provided to translate movement of elements in manipulator assembly 60 to catheter 16. Cartridge 62 receives and retains proximal end 38 of catheter 16. Cartridge 62 may include sliding blocks 64 each coupled to a corresponding steering wire 66 so as to permit independent tensioning of each wire 66. Movement of the blocks 64 is controlled by manipulator assembly 60 to cause tensioning of the wires 66 and thereby affect translation, deflection, and rotation of catheter 16.

A more complete description of various elements of an RCGS may be found in the following patent applications that are incorporated herein by reference in their respective entireties: International Patent Application Publication No. WO 2009/120982 published Oct. 1, 2009; U.S. Patent Application Publication No. 2009/0247942 published Oct. 1, 2009; U.S. Patent Application Publication No. 2009/0247944 published Oct. 1, 2009; U.S. Patent Application Publication No. 2009/0247993 published Oct. 1, 2009; U.S. Patent Application Publication No. 2009/0248042 published Oct. 1, 2009; U.S. Patent Application Publication No. 2010/0256558 published Oct. 7, 2010; and U.S. Patent Application Publication No. 2011/0015569 published Jan. 20, 2011. Further, although a particular embodiment of an RCGS 22 has been described and illustrated herein, it should be understood that RCGS 22 may assume a variety of different embodiments. For example, RCGS 22 may comprise any of the systems offered for sale by Hansen Medical, Inc. under the trademarks Magellan and Sensei. RCGS 22 may also comprise a magnetic navigation system such as the system offered for sale by Stereotaxis, Inc. under the trademark Epoch in which magnetic fields are used to guide an ablation catheter having a magnetic member that is responsive to the generation of the magnetic fields.

Display system 24 is provided to convey information to a clinician to assist in diagnosis and treatment. Display system 24 may comprise one or more conventional computer monitors or other display devices. Display system 24 presents a graphical user interface (GUI) to the clinician. The GUI may include a variety of information including, for example, an image of the geometry of tissue 12, electrophysiology data associated with the tissue 12, graphs illustrating voltage levels over time for various electrodes 42, 44, and images of catheter 16 and other medical devices and related information indicative of the position of catheter 16 and other devices relative to the tissue 12.

ECU 26 provides a means for controlling delivery of ablation energy by ablation catheter 16 to tissue 12 and for controlling the operation of various components of system 10 including catheter 16, ablation generator 18, RCGS 22, display system 24 and switch 50 of navigation system 20. ECU 26 may comprise one or more programmable microprocessors or microcontrollers or may comprise one or more ASICs. ECU 26 may include a central processing unit (CPU) and an input/output (I/O) interface through which ECU 26 may receive a plurality of input signals including signals generated by ablation generator 18, electrodes 42, 44 on catheter 16, patch electrodes 48 of system 20, and input control system 56 of RCGS 22 and generate a plurality of output signals including those used to control and/or provide data to catheter 16, ablation generator 18, display 24, switch 50 of system 20, and manipulator assembly 60 of RCGS 22.

Figure 3:
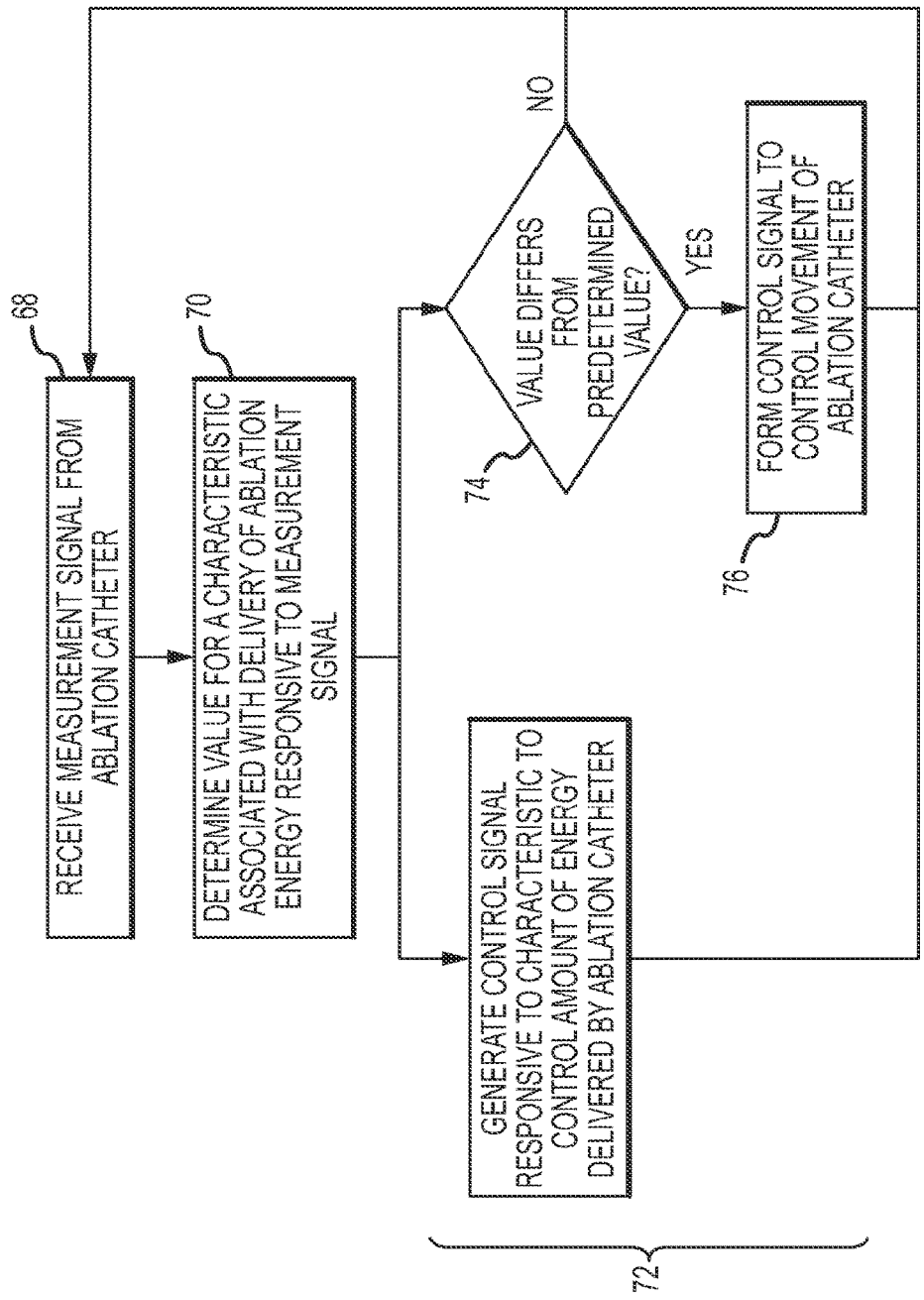
FIG. 3 is a flow chart diagram illustrating one embodiment of a method for controlling delivery of ablation energy from an ablation catheter to tissue in a body in accordance with the present teachings.

In accordance with the present teachings, ECU 26 may be configured with programming instructions from a computer program (i.e., software) to implement a method, such as a closed-loop feedback method, for controlling delivery of ablation energy from catheter 16 to tissue 12 in body 14. The program may be stored in a local memory associated with ECU 26, a remote memory accessible by ECU 26 over a telecommunications network (e.g., on a file server) or on a portable storage medium such as a compact disc or on other types of computer readable storage mediums. Referring to FIG. 3, the method may begin with the steps 68, 70 of receiving one or more measurement signals from catheter 16 and determining, responsive to the measurement signal, a value for a characteristic associated with the delivery of ablation energy to tissue 12.

In accordance with one embodiment of the invention, the characteristic may comprise a degree of contact between an ablation delivery element, such as electrode 42, on catheter 16 and tissue 12 and/or an amount of force applied by the ablation delivery element to tissue 12. The measurement signal may be generated by one or more tactile or force contact sensors on catheter 16 configured to detect a force applied to electrode 42 resulting from contact by electrode 42 with tissue 12 in order to assess the degree of mechanical coupling between catheter 16 and tissue 12. The contact sensors may generate signals indicative of a change in resistance, voltage, capacitance, impedance or a combination thereof. The sensors may comprise, for example, capacitance sensors that generate a signal indicative of a change in capacitance resulting from application of a force. The sensors may also comprise piezoelectric sensors that include a piezoelectric material (in the form of a wire, film or tubes, for example) and generate a signal indicative of a change in voltage resulting from placing the piezoelectric material under stress. The sensors may also comprise pressure sensitive conductive composite (PSCC) sensors (including, but not limited to, quantum tunneling conductive composite (QTC) sensors) in which the electrical resistance of the composite varies inversely in proportion to the pressure that is applied to the composite. Such sensors generate a signal indicative of a change in resistance or conductivity in the composite resulting from application of force. Additional information on exemplary sensor embodiments usable with the invention may be found in U.S. Patent Application Publication No. 2011/0022045, U.S. Patent Application Publication No. 2008/0161796, U.S. Patent Application Publication No. 2008/0015568, U.S. Patent Application Publication No. 2007/0123764 and U.S. Patent Application Publication No. 2007/0100332, the entire disclosures of which are incorporated herein by reference.

The sensors may also comprise a pair of optically interactive elements such as an optically interactive surface and one or more optic fibers configured to emit and receive light energy from the electromagnetic spectrum. The optically interactive surface has a known position relative to the ablation delivery element such that a change in position, configuration and/or orientation of the surface causes a change in the plane of reflection and a change in a characteristic of light (e.g., intensity, wavelength, phase, spectrum, speed, optical path, interference, transmission, absorption, reflection, refraction, diffraction, polarization and scattering) indicative of a force applied to the ablation delivery element by, for example, contact with tissue 12. The surface may be comprised of any material capable of reflecting or refracting light including, for example, polished metals. Refractive media (e.g., a lens or filter) or mediums (air, gel, or liquid including those dispersed or suspended in a solid or solid particulate) may be employed with surface. Additional information on exemplary optical sensing assemblies usable with the invention may be found in U.S. Patent Application Publication No. 2008/0249522, U.S. Patent Application Publication No. 2008/0275428 and International (PCT) Patent Application Publication No. WO 2010/078453, the entire disclosures of which are incorporated herein by reference.

In accordance with another embodiment, the degree of contact may be determined by determining the degree of electrical coupling between catheter 16 and tissue 12 using measurement signals generated by one or more of electrodes 40, 42 and indicative of impedance between the ablation delivery element and tissue 12. As discussed in U.S. Patent Application Publication No. 2010/0228247, U.S. Patent Application Publication No. 2009/0163904, and U.S. Patent Application Publication No. 2010/0168735, the entire disclosures of which are incorporated herein by reference, ECU 26 may enable generation of an excitation signal from a signal source (not shown) across a path from an electrode 42, 44 on catheter 16 to a return electrode located, for example, on catheter 16 or body 14. This signal induces a response signal along a path from the catheter electrode to another return electrode on catheter 16 or body 14 that is dependent on the complex impedance at the catheter/tissue interface. Conventional circuits may be used to resolve this signal into component parts for the complex impedance at the catheter/tissue interface allowing ECU 26 to determine values for one or more components of a complex impedance between the ablation delivery element and tissue 12. These components may including a resistance between the element and tissue 12, a reactance between the element and tissue 12, an impedance magnitude between the element and tissue 12 and an impedance phase angle between the element and tissue 12. ECU 26 may further compute a coupling index responsive to these components and possibly other measurements that are indicative of the degree of contact between the ablation delivery element and tissue 12.

In accordance with another embodiment, the characteristic associated with the delivery of ablation energy determined by ECU 26 may comprise a level of conductivity in tissue 12, change in amplitude of an electrogram, or another indicator of the quality of the lesion created by the delivery of ablation energy to tissue 12. The measurement signals use to determine this characteristic may include temperature measurements at the distal end 40 of catheter 16 using conventional temperature sensors on catheter 16 and/or impedance measurements using electrodes 42, 44. ECU 26 may use these signals alone or in combination with other parameters accessible through ablation generator 18 including the time duration of delivery of ablation energy and power levels.

In accordance with yet another embodiment, the characteristic associated with the delivery of ablation energy determined by ECU 26 may comprise an identity of a cardiac rhythm. The delivery of ablation energy has the potential to cause ventricular tachycardia or other arrhythmias. ECU 26 may identify the cardiac rhythm using electrogram readings obtained from measurement signals generated by electrodes 42, 44.

In accordance with yet another embodiment, the characteristic associated with the delivery of ablation energy determined by ECU 26 may comprise the presence or amount of particulates in the bloodstream. In some instances, ablation may result in dislodgement of particles that may be carried by the bloodstream to the brain and increase the risk of a stroke. The measurement signals used to determine this characteristic may include signals indicative of blood flow velocity in the blood vessels such as the basal cerebral arteries. These signals may be generated by ECU 26 or another device for processing images of the brain during an ablation procedure such as the intraoperative transcranial Doppler monitoring system offered for sale by Natus Medical, Inc. under the trademark Sonara.

In accordance with yet another embodiment, the characteristic associated with the delivery of ablation energy determined by ECU 26 may comprise the presence or amount of micro-bubbles in the bloodstream. In some instances, ablation may result in overheating of the blood and the generation of micro bubbles in the blood. The measurement signals used to determine this characteristic may include signals indicative of the presence or amount of micro bubbles in the bloodstream. These signals may be generated by ECU 26 or another device for processing images to identify the presence or amount of micro bubbles in the blood. The images may comprise intracardiac echocardiography (ICE) images generated by an ICE catheter.

In accordance with yet another embodiment, the characteristic associated with the delivery of ablation energy determined by ECU 26 may comprise a degree or type of motion of the body of a patient or a part of the body. For example and in some instances, cardiac ablation may impact the vagus and/or phrenic nerves which pass near the heart. Because the vagus and phrenic nerve affects the diaphragm and breathing, damage to one or both of the nerves can result in vibration of the diaphragm that may be sensed by a motion sensor and used to control further delivery of ablation therapy. As an alternative to a dedicated motion sensor, information regarding movement of the diaphragm or other respiratory motion indicative of nerve palsy can be obtained from signals indicative of such motion generated in the system offered for sale under the trademark EnSite™

NavX™ by St. Jude Medical referenced hereinabove. As another example and in some instances, during renal ablation the renal artery may spasm and clamp down onto the ablation catheter. This spasm or motion may be sensed by a motion sensor (e.g., near the stomach) and used to control further delivery of ablation therapy.

The method may continue with the step 72 of generating one or more control signals in response to the determined characteristic. In accordance with one aspect of the invention, a control signal may be used to control an amount of ablation energy delivered from the ablation delivery element to tissue 12. The control signals may be provided to radio frequency generator 48 to control the ablation signal provided to ablation catheter 16.

Figure 4:
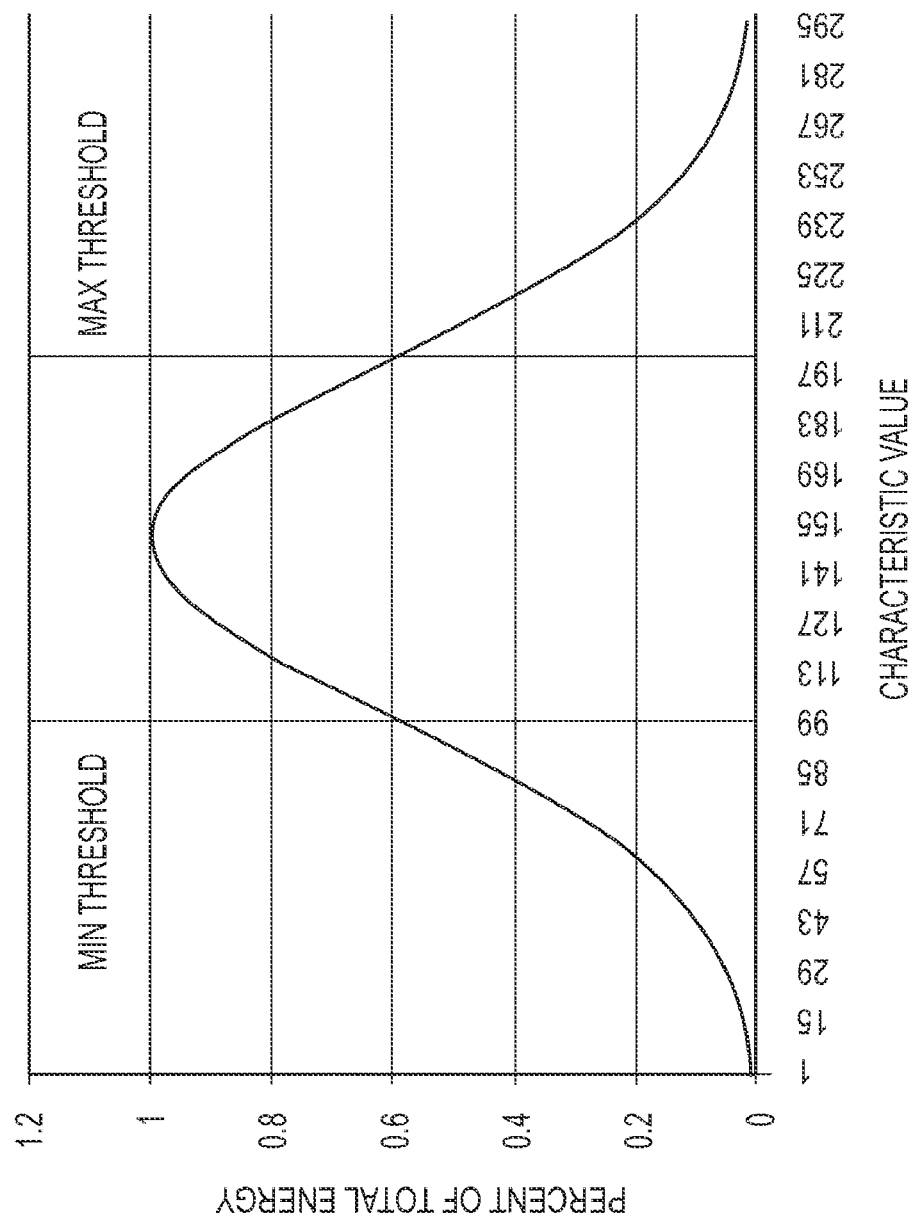
FIG. 4 is a plot diagram illustrating a function correlating a change in the amount of ablation energy generated in response to a change in the degree of contact between the ablation catheter and tissue in accordance with one embodiment of the present teachings.

Referring now to FIG. 4, one embodiment of a control function that may be implemented in ECU 26 to control the amount of energy delivered by catheter 16 in response to a determined value of a characteristic is illustrated. In the illustrated embodiment, the characteristic comprises the degree of contact between the ablation delivery element and tissue 12 which may be determined as described hereinabove. It should be understood, however, that similar functions may be used for other determined characteristics. The function may define minimum and maximum threshold values for the characteristic. Where the characteristic comprises the degree of contact between the ablation delivery element and tissue 12, the minimum threshold may represent insufficient contact or a lack of contact with tissue 12 while the maximum threshold may represent a level of contact that risks perforation of the tissue and, in the case of cardiac tissue, cardiac tamponade. In accordance with one aspect of the invention, the amount of energy varies in response to the determined value of the characteristic when the determined value of the characteristic meets a predetermined condition relative to at least one of the threshold values. Systems have been proposed previously that would control ablation energy in response to the degree of contact, but these systems rely on a relatively simple on/off control methodology in which ablation energy is delivered, at a presumably constant level, when the degree of contact is between minimum and maximum threshold values and delivery of energy ceases when the degree of contact is less than the minimum threshold value or greater than the maximum threshold value. These prior systems do not allow for optimization of energy delivery to tissue 12 and can result in undesirable amounts of energy applied when the degree of contact is near the threshold values as well as undesirable oscillation between disparate energy levels. As shown in FIG. 4, the inventor herein proposes a control function wherein the amount of energy delivered to tissue 12 continuously varies in response to the value of the degree of contact (or another characteristic) when the degree of contact is greater than or equal to the minimum threshold value or less than or equal to the maximum threshold value. By varying or titrating the amount of energy, finer, optimized control of ablation energy is achieved. In accordance with the illustrated embodiment, the amount of energy assumes a maximum value when the degree of contact is between the minimum and maximum threshold values and, in particular, when the degree of contact is midway between the minimum and maximum threshold values. Further, for values of the degree of contact including and between the minimum and maximum threshold values, the amount of energy assumes a minimum value when the degree of contact is at one or both of the threshold values and increase as the difference between the value of the degree of contact and either of the threshold values increases until reaching the maximum value at the midpoint of the two threshold values. In the illustrated embodiment, the amount of energy also varies in response to the degree of contact when the value of the degree of contact is less than the minimum threshold value or greater than the maximum threshold value. The amount of energy is higher, however, when the degree of contact is between the minimum and maximum threshold values than when the degree of contact is not between the threshold values (i.e., lower than the minimum threshold value or higher than the maximum threshold value). Further, the amount of energy decreases moving away from the threshold values when the degree of contact is not between the threshold values.

Although in the illustrated embodiment, the amount of energy varies on both sides of a threshold value, it should be understood that in an alternate embodiment the amount of energy may vary only when the degree of contact is between the threshold values and energy delivery may cease when the degree of contact is outside of the threshold values thereby allowing for optimized control of energy delivery only when contact is deemed sufficient to support delivery of ablation energy. Further, although the illustrated embodiment implements a Gaussian function to defines the amount of energy delivered to tissue 12, it should be understood that other control functions could be implemented that result in continuous variation of the amount of energy delivered to tissue 12 in response to the value of the degree of contact (or another characteristic). For example, a Sigmoid function could alternatively be employed where the amount of ablation energy delivered to tissue 12 constantly increases or decreases between (and even outside of) the thresholds.

Figure 5:
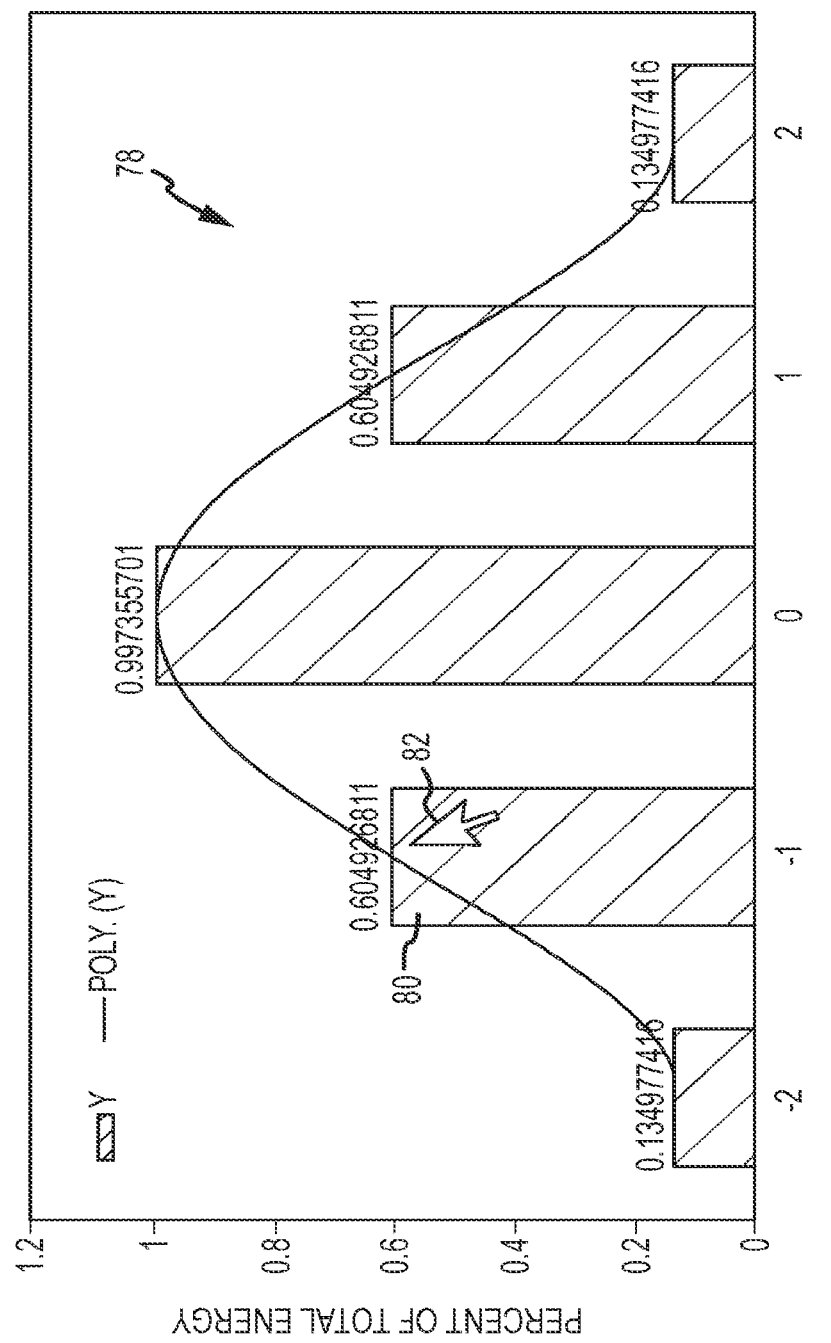
FIG. 5 is a diagrammatic view of a graphical user interface in accordance with one embodiment of the present teachings through which a clinician may establish a control function correlating a change in the amount of ablation energy generated in response to a change in the value of a characteristic.

In accordance with one embodiment of the invention, the control function implemented by ECU 26 is established by the clinician using an input device such as a graphical user interface on display system 24 or input system 58 of RCGS 22. Using the input device, the clinician may select from among a plurality of predetermined control functions stored in a memory associated with ECU 26. Alternatively, the clinician may create a control function by, for example, setting values for the amount of energy to be delivered by ablation catheter 16 in response to one or more values for the characteristic. For example, the clinician may establish energy amounts at the minimum and maximum threshold values for the characteristic and a midpoint between those threshold values. The amount of energy for other values of the characteristic not established by the clinician may be determined by ECU 26 using conventional interpolation methods (e.g. by computing a spline through the established values). Alternatively, the clinician may establish a constant amount of energy over one or more ranges of values for the characteristic. Referring to FIG. 5, for example, a graphical user interface 78 may display a bar 80 or another symbol representing the amount of energy to be delivered by ablation catheter 16 in response to a representative value of a characteristic such as the degree of contact. Using an input device (e.g., a mouse, touch screen display, etc.), the clinician may directly touch the applicable portion of the screen with his or her finger and/or move a cursor 82 to grab onto the top line of a bar 80 and raise or lower the bar 80 to thereby adjust the energy output for one or more values of a characteristic. In addition to the graphical representation, the amount of energy may be shown as a decimal percentage of total output. The amount of energy for other values of the characteristic not established by the clinician may again be determined by ECU 26 using conventional interpolation methods (e.g. by computing a smooth spline through the levels set by the clinician). The interface may allow the clinician to increase the number of bars 80 (or other symbols) through which the clinician may enter amounts of energy for additional values of the characteristic and additional detail to the control function. Further, although the illustrated embodiment shows a smooth function, the interface may allow the clinician to establish a hard transition either by modifying a threshold or allowing discontinuities in the control function. Accordingly, prior to implementing step 68, ECU 26 may be configured to perform the step of establishing a control function correlating values for the characteristic and amounts of energy to be delivered by catheter 16 to tissue 12. In one embodiment, this step may include the substeps of identifying a plurality of control functions correlating values for the characteristic and amounts of energy to be delivered by catheter 16 to tissue 12 and selecting one control function from the plurality of control functions in response to an input signal generated through a user interface. In another embodiment, this step may include the substeps of receiving one or more input signals through a user interface, each of the input signals setting an amount of energy for a selected value of the characteristic, and determining an amount of energy for unselected values of the characteristic (through, for example interpolation).

Referring again to FIG. 3, in accordance with another aspect of the invention, one or more control signals may also be provided to manipulator assembly 60 of RCGS 22 to control the position of catheter 16 relative to tissue 12 (e.g., to move catheter 16 nearer to tissue 12 or further away from tissue 12). In one embodiment, step 72 may include the substeps 74, 76 of comparing the determined value of the characteristic to a predetermined value and forming the control signal if the determined value of the characteristic meets a predetermined condition relative to the predetermined value. For example, if the characteristic is a degree of contact and the determined value indicates that the ablation delivery element on catheter 16 is further away from tissue 12 than desired as indicated by the predetermined value, a control signal may be provided by ECU 26 to manipulator assembly 60 and drive assembly 62 to move the ablation delivery element and increase the degree of contact with tissue 12. Similarly, if the determined value indicates that the ablation delivery element on catheter 16 has a degree of contact with tissue 12 that is greater than desired as indicated by the predetermined value, a control signal may be provided by ECU 26 to manipulator assembly 60 and drive assembly 62 to move the ablation delivery element and reduce the degree of contact with tissue 12. These steps and substeps can be performed repeatedly such that drive assembly 62 maintains substantially the same degree of contact between the ablation delivery element and tissue 12 over time in response to control signals generated by ECU 26.

A system 10 and method for controlling delivery of ablation energy from an ablation catheter 16 to tissue 12 in a body 14 in accordance with the present teachings is advantageous because the system and method enable finer control of the delivery of ablation energy to tissue in response to changes in various characteristics associated with the delivery of ablation energy to the tissue. As a result, delivery of ablation energy into the blood is minimized to reduce the risks of thrombus formation.

Although several embodiments of this invention have been described above with a certain degree of particularity, those skilled in the art could make numerous alterations to the disclosed embodiments without departing from the scope of this invention. All directional references (e.g., upper, lower, upward, downward, left, right, leftward, rightward, top, bottom, above, below, vertical, horizontal, clockwise and counterclockwise) are only used for identification purposes to aid the reader's understanding of the present invention, and do not create limitations, particularly as to the position, orientation, or use of the invention. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other. It is intended that all matter contained in the above description or shown in the accompanying drawings shall be interpreted as illustrative only and not as limiting. Changes in detail or structure may be made without departing from the invention as defined in the appended claims.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

What is claimed is:

1. A method for controlling delivery of energy to an electrode, comprising:
   delivering an amount of energy to the electrode;
   receiving, with a processor, a measurement signal indicative of an amount of particulates in a bloodstream of a patient in which the electrode has been inserted; and
   varying the amount of energy based on the measurement signal.

2. The method of claim 1, wherein the measurement signal includes a signal indicative of blood flow velocity in a blood vessel of the patient.

3. The method of claim 2, wherein the measurement signal indicative of blood flow velocity in the blood vessel of the patient is generated from an image of a brain of the patient.

4. The method of claim 1, wherein the method includes implementing a closed-loop feedback method for varying the amount of energy.

5. The method of claim 1, further comprising generating a control signal from the measurement signal.

6. The method: of claim 3, further comprising providing the control signal to a generator, the control signal being configured to cause die generator to vary the amount of energy.

7. The method of claim 1, further comprising causing a generator to vary the amount of energy in response to the measurement signal meeting a determined condition relative to a threshold value.

8. The method of claim 1, further comprising causing a generator to continuously vary the amount of energy in response to the measurement signal meeting a determined condition relative to a threshold value.

9. The method of claim 1 further comprising causing a generator to continuously vary the amount of energy in response to a change in the measurement signal when a value of the measurement signal is between a first threshold and a second threshold value.

10. The method of claim 1, wherein delivering the amount of energy to the electrode includes causing a generator to generate the amount of energy, the generator being configured to deliver the amount of energy to the electrode.

11. A method for controlling delivery of energy to an electrode, comprising: delivering an amount of energy to the electrode; receiving, with a processor, a measurement signal indicative of an amount of bubbles in a bloodstream of a patient in which the electrode has been inserted; and varying the amount of energy based on the measurement signal.

12. The method of claim 11 wherein the bubbles are caused from an overheating of blood in the patient with the electrode.

13. The method of claim 11, wherein the bubbles are identified from images taken of the patient.

14. The method of claim 13, wherein the images include intracardiac echocardiography (ICE) images.

15. The method of claim 14, wherein the ICE images are generated by an ICE catheter.

16. The method of claim 11, further comprising generating a control signal from the measurement signal.

17. The method of claim 16, further comprising providing the control signal to a generator, the control signal being configured to cause the generator to vary the amount of energy.

18. A system for controlling delivery of energy to an electrode, the system comprising: a processor; and non-transitory computer readable medium coupled with the processor, the non-transitory computer readable medium storing instructions executable by the processor to; cause a generator to deliver an amount of energy to an electrode disposed on a catheter; receive a measurement signal from a sensor, the measurement signal indicative of a motion of a body of a patient in which the electrode has been inserted; generate a control signal based on the measurement signal meeting a determined condition relative to a threshold value: and send the control signal to the generator, the control signal being configured to cause the generator to vary the amount of energy.

19. The system of claim 18 wherein; the measurement signal indicative of the motion of the body of the patient comprises at least one of a degree of motion and a type of motion; and the at least one of the degree of motion and the type of motion is indicative of damage caused to a nerve from a cardiac ablation performed by the electrode.

20. The system of claim 18 wherein the measurement signal indicative of the motion of the body of the patient is indicative of a respiratory motion of the patient; the respiratory motion of the patient is caused from nerve palsy resulting from a cardiac ablation performed by the electrode.

21. The system of claim 18 wherein the motion of the body of the patient is caused from a renal ablation performed by the electrode.

22. The system of claim 21, further comprising instructions executable by the processor to detect a renal artery spasm based on the measurement signal received from the sensor.

* * * * *